United States Patent
Santoli et al.

(10) Patent No.: US 7,875,164 B2
(45) Date of Patent: Jan. 25, 2011

(54) METHOD FOR USE OF AN ELECTROCHEMICAL SENSOR AND ELECTRODES FORMING SAID SENSOR

(75) Inventors: Eduardo Santoli, Noiraigue (CH); Philippe Rychen, Muespach le Haut (FR); Jean Gobet, Corcelles (CH); Remo Pfändler, Goldach (CH); Paul Bitsche, Hohenems (AT)

(73) Assignees: Adamant Technologies SA, La Chaux-de-Fonds (CH); Züllig AG, Rheineck (CH)

( * ) Notice: Subject to any disclaimer, the term of this patent is extended or adjusted under 35 U.S.C. 154(b) by 258 days.

(21) Appl. No.: 11/911,926

(22) PCT Filed: Apr. 19, 2006

(86) PCT No.: PCT/EP2006/061681

§ 371 (c)(1),
(2), (4) Date: Nov. 7, 2007

(87) PCT Pub. No.: WO2006/111550

PCT Pub. Date: Oct. 26, 2006

(65) Prior Publication Data

US 2008/0202944 A1     Aug. 28, 2008

(30) Foreign Application Priority Data

Apr. 22, 2005     (EP) .................................. 05103304

(51) Int. Cl.
*G01N 33/18* (2006.01)
(52) U.S. Cl. ........................................ 205/743; 205/775
(58) Field of Classification Search ...... 205/775–794.5, 205/743, 782; 204/400–420, 431–435
See application file for complete search history.

(56) References Cited

U.S. PATENT DOCUMENTS 4,457,808 A  *  7/1984  Taylor et al. ............. 205/782.5

(Continued)

FOREIGN PATENT DOCUMENTS

EP     0605882     7/1994

(Continued)

OTHER PUBLICATIONS

Kim et al., Manipulation of microenvironment with a built-in electrochemical actuator in proximity of a dissolved oxygen microsensor, IEEE Sensors Journal, vol. 4, No. 5, 2004).*

(Continued)

*Primary Examiner*—Alexa D Neckel
*Assistant Examiner*—Jennifer Dieterle
(74) *Attorney, Agent, or Firm*—Townsend M. Belser, Jr.; Nexsen Pruet, LLC

(57) ABSTRACT

A method for in situ self-calibrating of an electrochemical sensor for measuring the concentration of one or more species in an aqueous medium. The method includes: taking a first measurement of the current of a working electrode representative of the concentration of dissolved oxygen in the medium, applying an anode current of predetermined density and duration to a generating electrode to produce a defined increase in the local concentration of the dissolved oxygen, taking a second measurement of the current of the working electrode representative of the concentration of oxygen after applying the anode current to the generating electrode, and computing from the first and second measurements a calibration factor for one or more species that relates the oxygen concentration of the medium to be analyzed and the actually measured current between the working electrode and its counter electrode.

6 Claims, 3 Drawing Sheets

U.S. PATENT DOCUMENTS

| | | |
|---|---|---|
| 5,230,785 A | 7/1993 | Yager |
| 5,597,463 A | 1/1997 | Birch et al. |
| 5,900,128 A | 5/1999 | Gumbrecht et al. |
| 2001/0001441 A1 | 5/2001 | Zdunek et al. |
| 2002/0137991 A1* | 9/2002 | Scarantino et al. .......... 600/300 |
| 2003/0173233 A1 | 9/2003 | Vincent |
| 2004/0154934 A1* | 8/2004 | Gobet et al. ............. 205/787.5 |

FOREIGN PATENT DOCUMENTS

| | | |
|---|---|---|
| EP | 1557665 | 7/2005 |
| FR | 2779523 | 12/1999 |
| GB | 2290617 | 1/1996 |
| JP | 2000 093907 | 4/2000 |
| RO | 117948 | 9/2002 |
| RU | 2207558 | 10/2002 |
| WO | WO 97/42497 | 11/1997 |
| WO | WO 02/095387 | 11/2002 |

OTHER PUBLICATIONS

XP002369703.
International Search Report PCT/EP2006/061681 related to subject application.
European Search Report EP05103304 related to subject application.
English language Abstract of JP 2000 093907.

* cited by examiner

METHOD FOR USE OF AN ELECTROCHEMICAL SENSOR AND ELECTRODES FORMING SAID SENSOR

BACKGROUND OF THE INVENTION

1) Field of the Invention

The present invention relates to electrochemical sensors intended for measuring the concentration of a chemical substance in an aqueous medium. Such devices find a particularly interesting but not exclusive application, to the detection of the amount of dissolved oxygen in water, particularly in basins of sewage works.

The invention more particularly relates to a method for self-calibrating an electrochemical sensor and to a method for self-cleaning this sensor. The invention also relates to particularly suitable electrodes for forming this sensor.

2) Description of Related Art

The electrochemical sensors of the aforementioned type necessarily include a working electrode, a reference electrode and a counter electrode. Another type of such sensors which further include a so-called generating electrode and its counter electrode, is also known. By adding both of these latter electrodes, the effect of which is to generate changes in the concentration of the species present in solution, it is possible to locally control the environment of the working electrode.

For example, the pH of the solution may be locally changed by applying a current to the generating electrode. A cathode current will cause the production of $OH^-$ ions (the pH then becoming more basic) and conversely, an anode current will cause the production of $H^+$ ions (the pH then becoming more acidic). A counter electrode associated with the generating electrode, a counter electrode associated with the working electrode and a reference electrode are required for making a complete sensor.

It will easily be understood that it is particularly advantageous to use, as a working electrode, electrodes of very small dimensions, not only because this allows the gap between the generating electrode and the working electrode to be reduced, but also because the effects of the turbulence of the liquid at the cell are found to be minimized. Such electrodes of small dimensions are indifferently called subsequently in the description, "micro-electrodes" or "micro-discs", this last name being due to the fact that the micro-electrodes are most often of a circular shape.

Document WO 02/095387 describes a sensor as mentioned earlier and illustrated in FIG. 1. It uses an electrically conducting substrate 10, advantageously made in doped silicon and the lower face of which is covered with a metallization layer 11. Its upper face is covered with a passivation layer 12 formed by stacking two sublayers of $SiO_2$ and $Si_3N_4$, known to have excellent stability in an aqueous medium.

The passivation layer 12 is provided with circular apertures 13. Its upper face and the apertures 13 are covered with a conducting layer 14 bearing reference 16 when it is on the layer 12 and reference 18 when it forms a micro-disc lying on one of the circular apertures 13. The layer 14 is pierced with a network of annular apertures 19 each surrounding one of the micro-discs 18.

The layer 16 forms the generating electrode whereas all the micro-discs 18, electrically connected in parallel with each other, form together the working electrode of the system.

The electrochemical sensors find an interesting application in the measurement of the concentration of dissolved oxygen in basins of sewage works. Indeed, waste water is treated by means of bacteria which are very sensitive to this dissolved oxygen concentration. The information provided by the sensors provides a control on an aeration system of the basin so that the conditions are favorable to bacteria. However, the sensors present on the market do not give satisfactory results, notably because of various contaminations and organic materials which are deposited on the electrode, thereby changing its sensitivity. With conventional sensors, for controlling contamination, one generally resorts to mechanical methods of the pulsed air, pressurized water jet, abrasion type methods which all have a lot of drawbacks.

In order to remove contamination from the surface of the sensor, the application filed under number EP 04 405039.1 proposes the use of a diamond-based generating electrode. When a voltage is applied to it, this electrode generates strongly oxidizing species, such as hydroxyl radicals, capable of efficiently burning organic materials.

However, with the effect obtained by these oxidizing species, it is not possible to totally prevent any contamination. Over the course of time, the sensor is gradually affected, which deteriorates the accuracy of the measurement.

SUMMARY OF THE INVENTION

One of the objects of the present invention is therefore to solve the aforementioned problem by proposing a sensor for which accuracy is not dependent on contamination phenomena.

More specifically, the invention relates to a method for self-cleaning a working electrode of an electrochemical sensor, including one working electrode of the micro-disc type and its counter electrode, and a reference electrode connected to a potentiostat, on the one hand, and a generating electrode in diamond doped with boron and its counter electrode connected to a current source on the other hand. The set of electrodes is further connected to an electronic control and measuring unit.

Advantageously, the method comprises the following steps:

application of an anode current to the generating electrode, and application of a cathode current to the generating electrode.

The self-cleaning method may precede a method for measuring at least one dissolved species in an aqueous medium. In this case, the working and reference electrodes are disconnected from their power supply during the self-cleaning step.

Also in order to avoid deterioration of the accuracy of the measurement, the invention relates to a method for self-calibrating in situ an electrochemical sensor as defined above and intended to measure the concentration of at least one dissolved species in an aqueous medium.

The self-cleaning method according to the invention comprises the following steps:

first measurement of the current of the working electrode representative of the concentration of dissolved oxygen in the medium before applying a current to the generating electrode, application of an anode current with determined density and duration to the generating electrode producing a defined increase in the local concentration of dissolved oxygen, second measurement of the current of the working electrode representative of the oxygen concentration after applying a current to the generating electrode, and computation, from said first and second measurements, of a calibration factor of said one or more species, which links the oxygen concentration of the medium to be analyzed and the current actually measured between the working electrode and its counter electrode.

Advantageously, the step for applying an anode current has sufficiently short duration so as to get rid of the influence of the hydrodynamic conditions of the medium. This duration is less than 500 ms, more particularly, less than 400 ms.

In a particularly interesting application, the electrochemical sensor mentioned in connection with the methods above, is intended to measure the concentration of dissolved oxygen in an aqueous medium.

Moreover, polymer coatings are generally deposited on the electrical contacts of the generating electrode and on the edges of the substrate. Now, radicals produced by the diamond electrode etch the polymer coatings, at the interface with the diamond electrode, located in contact with the solution, i.e. at the location through which the current flows.

The object of the present invention is also to provide a sensor, for which the structure of the working electrode may avoid the drawbacks due to various contaminations, without damaging the components of the sensor.

More specifically, the invention relates to a chip intended to be integrated into an electrochemical sensor in order to measure the concentration of a dissolved species in an aqueous medium. This chip includes:

a substrate made in an electrically conducting material, a working electrode borne by said substrate and formed with a plurality of electrically conducting micro-discs connected to each other, a generating electrode borne by said substrate and close to the working electrode, said generating electrode being formed with a diamond plate made conductive by doping, pierced with circular apertures positioned so that each of them is concentric with a micro-disc, and being provided with at least one electric contact, and a polymer coating deposited on said electrical contact and on the edges of the substrate.

According to the invention, the chip further comprises a protective layer positioned on the generating electrode and inserted between the upper face of the diamond electrodes and the polymer coating, so as to suppress any direct interface between the coating and the generating electrode, which may be in contact with the medium.

BRIEF DESCRIPTION OF THE DRAWINGS

Other details of the invention will become more clearly apparent upon reading the description which follows, made with reference to the appended drawing wherein.

DETAILED DESCRIPTION OF THE INVENTION

In the description hereinbelow, a negative voltage refers to a cathode potential and a positive voltage refers to an anode potential.

Figure 2:
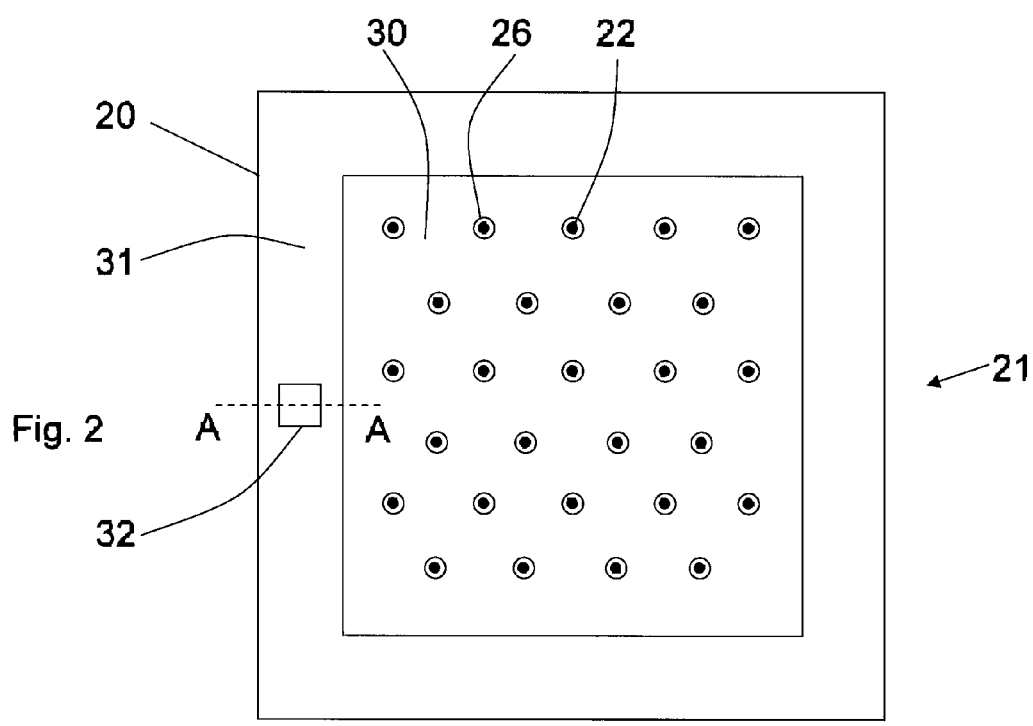
Figure 3:
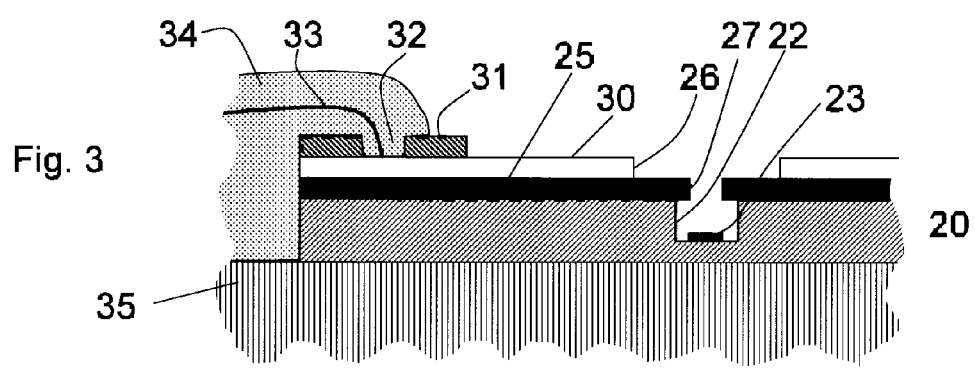

FIGS. 2 and 3 illustrate a chip 21. It has an electrically conducting substrate 20 which appears as e.g. a square plate, typically with a side from 2 to 10 mm and a thickness of 0.5 mm. Advantageously, this plate is in silicon made conductive by doping according to techniques well known to one skilled in the art. It is laid on a support 35 made in insulating polymer.

The substrate 20 on its upper face is pierced with a regular network of substantially cylindrical cavities, with an axis perpendicular to the plane of the substrate. Typically, the cavities have a diameter from 10 to 20 µm, a depth from 2 to 20 µm and are spaced apart from each other by about 40 to 400 µm.

The bottom of each cavity 22 is partly covered with metallization 23 which has a diameter less than that of the cavity 22, by 0.5 to 5 µm. The whole of the metallization 23 forms the working electrode of the system. Advantageously, a metal deposit may be made on the metallization 23 by galvanic growth.

The upper face of the substrate 20 is covered with an insulating layer 25, a so-called passivation layer, which for example is formed with a stack of two sublayers of $SiO_2$ and $Si_3N_4$, and it has a thickness from about 0.1 to 1 µm. This layer is pierced with a regular network of circular through-apertures 27 centered on the cavities 22 with a diameter less than that of the cavities.

The structure which has just been described is completed by a generating electrode 30, which may be in diamond, positioned around measuring electrodes according to the teaching of document WO 02/095387 and of application EP 4 405039.1.

More particularly, the electrode 30 is formed with a thin layer of diamond made conductive by doping, which is pierced with circular apertures 26 with a diameter larger than that of the cavities 22 and positioned so that each aperture 26 is concentric with a micro-electrode. Advantageously, the diamond used for forming the electrode is doped with boron.

Figure 1:
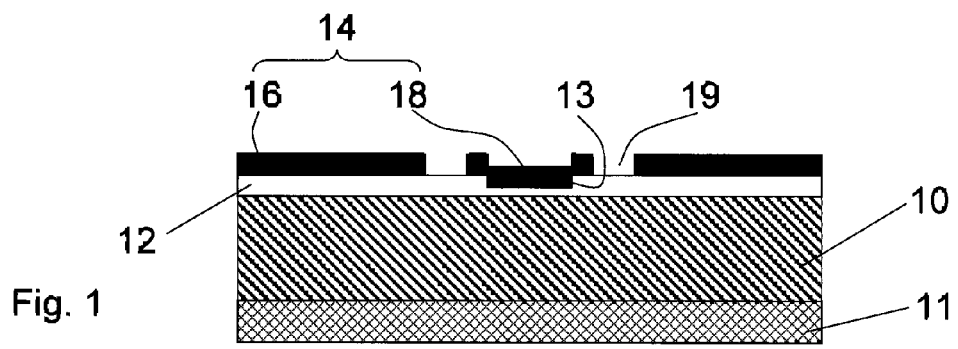
FIGS. 1, 2 and 3 are top and sectional views of a system of electrodes according to the invention, respectively.

Alternatively, the working and generating electrodes may be made according to the structure illustrated in FIG. 1.

When a voltage is applied to the electrode 30, strongly oxidizing species such as hydroxyl radicals may thereby be generated. As explained in the introduction, the latter may have a detrimental action on polymer coatings 34, for example silicone polymers, generally deposited on the electrical contacts of the generating electrode, more specifically at the interface between the coating 34 and the diamond layer 30 in contact with the medium.

In order to avoid these effects, a protective layer 31 is deposited on the diamond generating electrode 30 prior to the coating 34, so that there no longer exists any direct interface between the coating 34 and the diamond layer 30. This protective layer is made in an electrically insulating inorganic material such as $SiO_2$ or $Si_3N_4$, which further has excellent stability in an aqueous medium. The layer 31 has a thickness between 0.1 and 0.5 µm. It is deposited and conformed according to techniques known to one skilled in the art.

Advantageously, the protective layer 31 is located at the periphery of the electrode 30 and forms a frame so as to cover the components to be protected. It comprises apertures 32 required for electrical connection with the generating electrode 30. In order to improve the electric contact with the electrode 30, a metal contact frame, not shown, may be deposited by evaporation on a protective layer 31 which is provided with several apertures 32. The contact frame may also be made separately and then bonded to the electrode 30, at the apertures 32 with a conductive adhesive.

The polymer coating 34 is then deposited on the electrical contacts, and, if there is one, on the contact frame. As this may be seen in FIG. 3, the coating juts out over the protective layer 31 and also covers the side surfaces of the chip 21.

Figure 4:
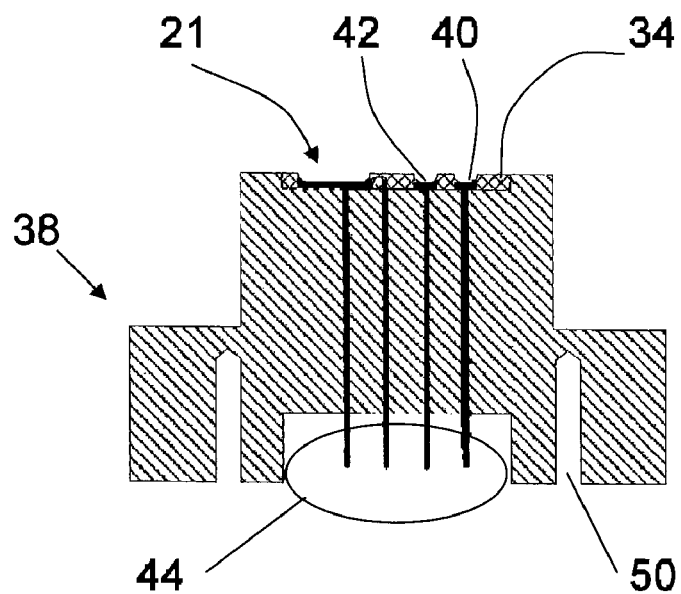
FIGS. 4 and 5 illustrate the application of the system of electrodes in a measuring device according to the invention.

The chip 21 described above therefore comprises a working electrode (the whole of the metallizations 23) and a generating electrode 30. It is integrated into a measuring head 38 illustrated in a sectional view in FIG. 4. The measuring head 38 further includes a counter electrode for the working electrode 40 and a reference electrode 42. The head 38 is made in a non-metal material of the non-conductive polymer type. The head 38 may also include a counter electrode for the generating electrode, but it will be understood hereafter why it does not appear in the described embodiment.

The areas of the electrodes intended to be contact with the medium to be analyzed are flush with the surface of the measuring head 38 and are located at a short distance from each other. Connecting components 44 cross the measuring head in order to connect the electrodes to the electronic control, measuring unit interfaced with the outside world (display, recording, etc.).

To summarize, it will be retained that the generating electrode and its counter electrode are connected to a current source, whereas the working electrode and its counter electrode on the one hand, and the reference electrode on the other hand, are connected to a potentiostat which allows a voltage to be imposed between the electrodes and thus measurement of the current flowing between the working electrode and its counter electrode at a determined voltage.

The counter electrode of the working electrode 40 is advantageously made in a conductive and chemically stable material, such as stainless steel, gold, or platinum. Its surface area is typically 100 times larger than that of the micro-discs of the working electrode 23. The reference electrode 42 is selected depending on the targeted application. For measuring the concentration of oxygen in an aqueous medium, an electrode of the Ag/AgCl type is generally preferred.

Figure 5:
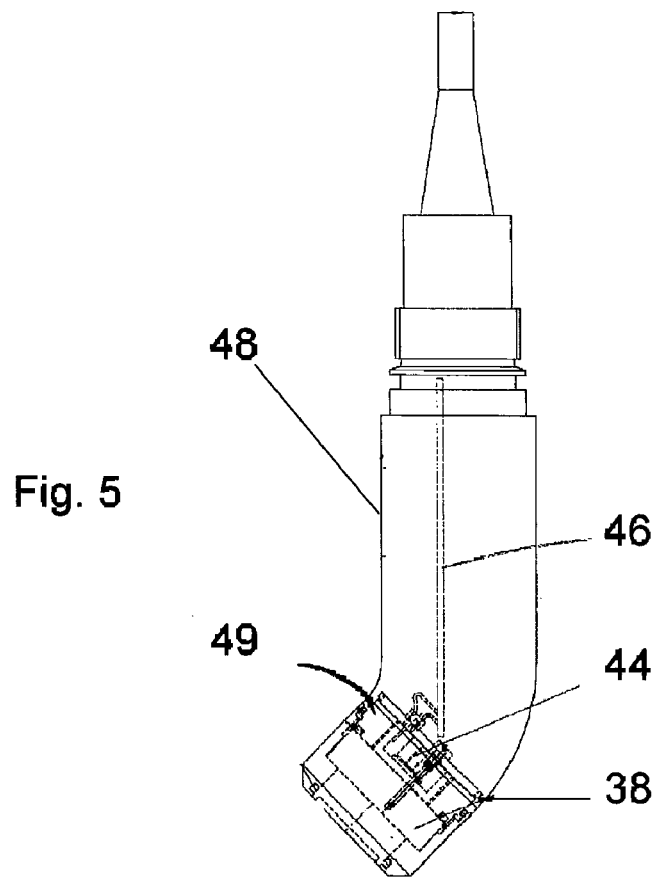

As indicated above for the chip 21, a layer of polymer material 34 is deposited on the edges of the substrates of the electrodes;

The measuring head 38 is sealably mounted to the end of a probe body 48, generally of tubular shape, visible in FIG. 5. In order to ensure that the connection components 44 of the head 38 are properly positioned relatively to the electronic unit 46 which is placed in the probe body, the head 38 is provided with positioning holes 50 which cooperate with lugs positioned in the body 48. It is thus very easy to replace the measuring head 38 if need be. The measuring head is then attached to the body of the probe by means of a ring 49 which is screwed onto the body of the probe so as to provide the seal of the assembly.

In an illustrated advantageous alternative, the probe body 48 is made in a metal material, such as stainless steel, and is used as a counter electrode for the generating electrode. Optionally, the body 48 is used as a counter electrode for the generating electrode and/or for the working electrode. The body 48 may also include a non-metal portion and a metal portion, the latter being used as a counter electrode.

The end of the probe body 48 which receives the measuring head 38 is tilted by an angle between 0 and 90°, preferably between 30 and 60°, preferably of the order of 45°, relatively to the remainder of the body 48. As the latter is immersed vertically into the liquid to be analyzed, the angle which its end has, allows the hydrodynamic conditions to be improved around the measuring head 38, particularly when the medium is stirred.

A method for using the electrochemical sensor which has just been described is explained hereafter, particularly with reference to an application to the measurement of dissolved oxygen in an aqueous medium.

The amperometric measurement of concentration of dissolved oxygen in an aqueous medium is achieved by applying an adequate reduction potential between the working electrode and the reference electrode. A reduction current is then generated, proportional to the concentration of dissolved oxygen in the liquid flowing between the working electrode and its counter electrode. The current in the working electrode may then be measured, this current being representative of the oxygen concentration of the medium.

A self-calibrating procedure, an example of which will be provided below, provides effective compensation of the drifts due to sensitivity losses of the working electrode. This in situ procedure is based on a change in the local concentration of dissolved oxygen, obtained by means of suitable changes in the polarization of the generating electrode which cause electrolysis of water according to the reaction:

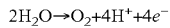

$$2H_2O \rightarrow O_2 + 4H^+ + 4e^-$$

This reaction locally changes the dissolved oxygen concentration in a specific way and regardless of the oxygen content of the surrounding medium. Indeed, the density and the application time of the current received by the generating electrode provide control of the production of oxygen.

With the difference between the responses of the working electrode before and after the production of oxygen by the generating electrode, the calibration factor may be inferred. The latter represents the sensitivity of the sensor and provides for a given sensor, a proportionality coefficient between the oxygen concentration of the medium to be analyzed and the actually measured current between the working electrode and its counter electrode.

Generally, the time during which the dissolved oxygen concentration is locally increased, depends on the stirring conditions of the medium.

Figure 6:
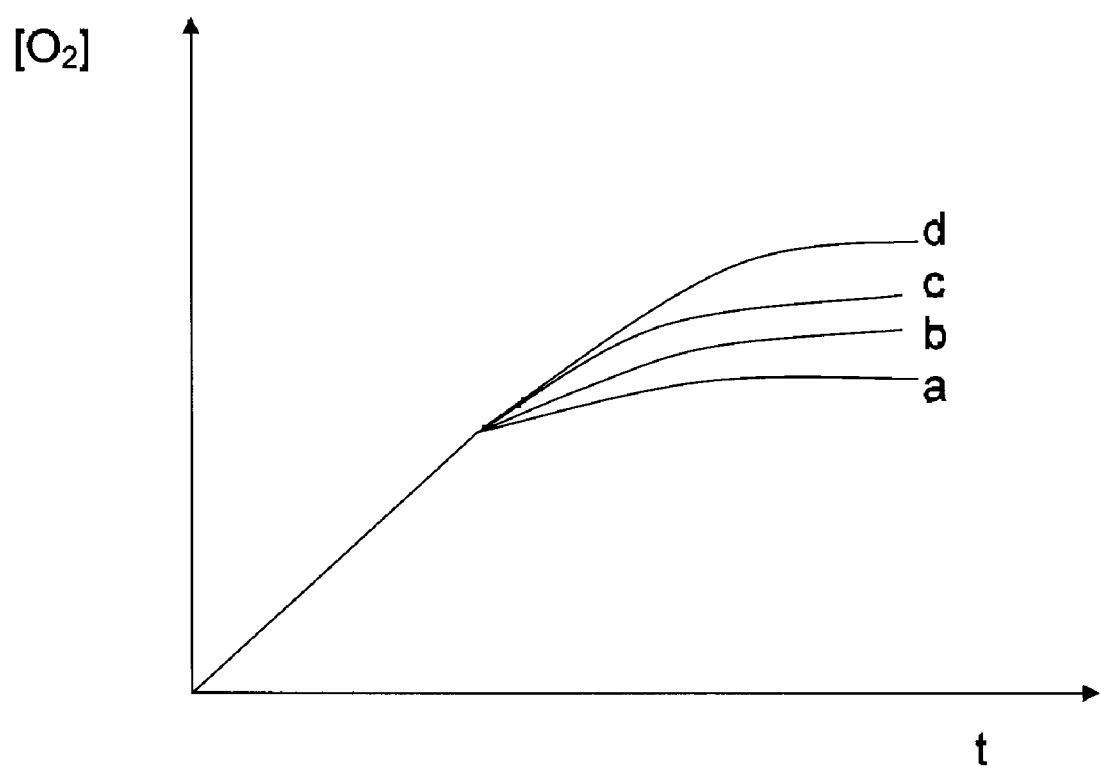
FIG. 6 illustrates the change in the concentration of dissolved oxygen versus time upon production of oxygen by the generating electrode, for different hydrodynamic conditions.

As shown in FIG. 6, which illustrates on curves a to d, the change in the oxygen concentration versus time under different stirring conditions, it was surprisingly seen that for a chip 21 provided with micro-discs, the concentration increases during the first instants of oxygen production linearly, without the hydrodynamic conditions having any influence. This linear phase lasts for about 500 ms. Thus, if the electrolysis current is only applied to the generating electrode for a reduced time, stirring of the medium does not perturb the oxygen concentration in the diffusion area and it is then possible to specifically measure the current generated by the oxygen actually produced by the generating electrode and to compute a calibration factor.

In a low conductivity medium, the electric field generated by the generating electrode may perturb the behavior of the reference electrode during self-calibration, if, during this procedure, measurement is performed simultaneously with operation of the generating electrode. In order to overcome this drawback, the self-calibration measurement is performed just after stopping the power supply of the generating electrode, on one point or by averaging the values obtained in a certain range, as this is seen hereinbelow. However, a measurement may be carried out while applying a current to the generating electrode.

Although a self-calibrating procedure allows compensation of possible drifts, due to fouling of the micro-electrodes, it is nevertheless of interest to be able to retain good sensitivity of the working electrode. This is obtained by a self-cleaning operation, performed in situ, and made possible by the properties of the boron-doped diamond of the generating electrode. This operation may also be performed with a preventive purpose.

Self-cleaning is obtained by the conjunction of several effects caused by applying to the diamond electrode currents with different polarity and density. First of all, an anode current causes a production of H$^+$ ions, which acidifies the aqueous medium close to the electrode. Thus, scale type deposits (calcium carbonate, magnesium oxides) are dissolved. Further, this type of current applied on a boron-doped diamond electrode causes a production of strongly active species such as hydroxyl radicals which degrade the organic deposits such as bio-films, and have biocidal activity.

Further, applying a cathode current causes the production of $OH^-$ ions which makes the aqueous medium basic close to the electrode. Thus, an alternation of anode/cathode currents causes a strong variation of the pH close to the diamond electrode, thereby preventing formation of a bio-film.

The self-cleaning step is applied at defined intervals, so that the oxygen produced during applying an anode current does not perturb subsequent measurements.

Different procedures are defined, each comprising a detailed series of sequences performed in a determined order in order to achieve the self-cleaning, self-calibrating and measuring step.

The electronic control unit 46 mentioned above, further comprises a programmed microprocessor for handling:
- the duration of the different steps,
- the potential differences between the working electrode and the reference electrode,
- measuring under a determined potential difference and as imposed by the potentiostat, the current which flows through between the working electrode and its counter electrode,
- the current applied between the generating electrode and its counter electrode, and
- the disconnection of the working and reference electrodes during the production of oxygen of the self-cleaning phase.

The other components of the electronic control unit 46 are perfectly accessible to one skilled in the art and are therefore not described here in detail.

At defined intervals, the current flowing between the working electrode and its counter electrode is measured and the concentration of dissolved oxygen is computed by means of the calibration factor determined beforehand. As an example, a typical measuring procedure, optionally comprising a mild self-cleaning step, includes the following sequences.

Waiting and mild self-cleaning:
  i. the working and reference electrodes are disconnected from their power supply, for a time typically between 0 and 60 s, more particularly 15 s.
  ii. mild self-cleaning is obtained by applying an anode current with a density typically between 0.5 and 2 $mA/cm^2$, more particularly 1 $mA/cm^2$, for a period ranging from 0.5 to 5 s, typically 1 s, starting immediately after the disconnection mentioned in point i. The remaining time for this step allows the oxygen produced at the generating electrode to be dispersed by diffusion into the medium.

Activation of the working electrode:
  i. an anode activation is obtained by applying a voltage typically between 200 and 1,500 mV, more particularly 500 mV, for a time typically between 0.1 and 30 s, more particularly 3 s.
  ii. a cathode activation is obtained by applying a voltage typically between −200 and −1,500 mV, more particularly −1,100 mV for a time typically between 0.1 and 10 s, more particularly 1 s.

Measurement and computation
  i. stabilization is obtained by applying to the working electrode a voltage typically between −500 and −1,200 mV, more particularly −900 mV for a time typically between 0.1 and 60 s, more particularly 8 s.
  ii. measurement and determination of the average current flowing between the working electrode and its counter electrode are conducted under a voltage typically between −500 and −1,300 mV, more particularly −900 mV, for a time between 0.1 and 30 s, more particularly 2 s.
  iii. the concentration of dissolved oxygen is computed from the current determined in the previous step and by means of the calibration factor predetermined according to the procedure provided above.

Such a measuring procedure is repeated at a frequency of typically 0.5 to 5 times per minute according to the values of the parameters defined above, more particularly 2 measurements per minute.

A self-calibration procedure typically comprises the following steps:

Waiting:
  i. the working and reference electrodes are disconnected from their power supply, for a time typically between 0 and 60 s, more particularly 15 s.

Activation of the working electrode:
  i. an anode activation is obtained by applying a voltage typically between 200 and 1,500 mV, more particularly 500 ms for a time typically between 0.1 and 30 s, more particularly 3 s.
  ii. a cathode activation is obtained by applying a voltage typically between −200 and −1,500 mV, more particularly −1,100 mV for a time typically between 0.1 and 10 s, more particularly 1 s.

Measurement of the oxygen concentration after applying a current to the generating electrode:
  i. stabilization is obtained by applying to the working electrode a voltage typically between −500 and −1,300 mV, more particularly −900 mV for a time typically between 0.1 and 60 s, more particularly 8 s.
  ii. a measurement and determination of the average current flowing between the working electrode and its counter electrode are conducted under a voltage typically between −500 mV and 1,300 mV, more particularly −900 mV, for a time typically between 0.1 and 30 s, more particularly 2 s.

Applying a self-calibration current to the generating electrode so as to produce a defined increase in the local concentration of dissolved oxygen:
  i. an anode current with a density typically between 0.1 and 10 $mA/cm^2$, more particularly 1 $mA/cm^2$, is applied for a time typically 0.1 and 1 s, more particularly 0.4 s.

Measuring the oxygen concentration after applying a current to the generating electrode:
  i. stabilization is obtained by applying to the working electrode a voltage typically between −500 and −1,300 mV, more particularly −900 mV, for a time typically between 0.01 and 0.1 s, more particularly 0.04 s.
  ii. measurement and determination of the average current flowing between the working electrode and its counter electrode are conducted under a voltage typically between −500 and −1,300 mV, more particularly −900 mV, for a time typically between 0.01 and 0.2 s, more particularly 0.08 s.
  iii. a new calibration factor for the working electrode is computed from the difference of the measurements before and after applying the self-calibration current on the auxiliary electrode.

Such a self-calibrating procedure is repeated at a frequency from 0.1 to 48 times per day, typically once a day.

A self-cleaning procedure typically comprises the following steps:
  i. applying an anode current to the generating electrode with a density typically between 0.5 and 100 mA/cm$^2$, more particularly 2 mA/cm$^2$, for a time typically between 0.5 and 60 s, more particularly 3 s,
  ii. applying a cathode current to the generating electrode with a density typically between 0.5 and 5 mA/cm$^2$, more particularly 2 mA/cm$^2$, for a time typically between 0.5 and 60 s, more particularly 3 s, and
  iii. repeating both preceding steps 1 to 30 times, more particularly 3 times.

Such a self-cleaning procedure is repeated at a frequency from 10 to 200 times per day, typically 100 times a day.

Thus, different particularly advantageous in situ self-calibrating, self-cleaning and measuring procedures are proposed with which good accuracy of an electrochemical sensor may be retained while avoiding the influence of any contamination due to the measurement medium. Moreover, the electrochemical sensor according to the invention allows self-cleaning, while preventing the oxidizing species from etching constitutive components of the sensor.

The present invention is not limited to an electrochemical sensor measuring the concentration of dissolved oxygen in a medium. Indeed, it is possible to establish a correlation between the measured currents for different analyzed species. Thus, from the oxygen produced by the generating electrode, it is possible to determine a self-calibration factor in order to allow the sensor to measure the concentration of a dissolved species other than oxygen, for example chlorine or ozone.

The invention claimed is:

1. An in situ self-calibrating method for an electrochemical sensor configured to measure the concentration of at least one dissolved species in an aqueous medium,
    said sensor including a working electrode of micro-disc type and its counter electrode, and a reference electrode, connected to a potentiostat on the one hand, and a generating electrode and its counter electrode connected to a current source on the other hand, these electrodes defining a set being further connected to an electronic control unit,
    said method comprising the following steps:
        a first measurement of the current of the working electrode representative of the concentration of dissolved oxygen in the medium before applying a current to the generating electrode,
        applying an anode current with determined density and duration to the generating electrode to produce a defined increase in the local concentration of dissolved oxygen,
        a second measurement of the current of the working electrode taken after said duration and representative of the concentration of oxygen after the application of said anode current to the generating electrode, and
        computing from said first and second measurements, a calibration factor for said at least one dissolved species, which relates the oxygen concentration of the medium to be analyzed and the actually measured current between the working electrode and its counter electrode.

2. The self-calibrating method according of claim 1, wherein said sensor is configured to measure the concentration of dissolved oxygen in an aqueous medium.

3. The self-calibrating method of claim 1, wherein the duration for applying said anode current has a value greater than zero but less than 500 ms, more particularly less than 400 ms, in order to get rid of the influence of the hydrodynamic conditions of the medium.

4. The self-calibrating method according of claim 3, wherein said sensor is configured to measure the concentration of dissolved oxygen in an aqueous medium.

5. The self-calibrating method of claim 3 further comprising forming the sensor by positioning the generating electrode around the working electrode.

6. The self-calibrating method according of claim 5, wherein said sensor is configured to measure the concentration of dissolved oxygen in an aqueous medium.

* * * * *